United States Patent
Mattiuzzi

(10) Patent No.: US 8,155,406 B2
(45) Date of Patent: Apr. 10, 2012

(54) IMAGE PROCESSING SYSTEM, PARTICULARLY FOR USE WITH DIAGNOSTIC IMAGES

(75) Inventor: Marco Mattiuzzi, Grassina Bagno a Ripoli (IT)

(73) Assignee: Bracco Imaging S.p.A., Milan (IT)

( * ) Notice: Subject to any disclaimer, the term of this patent is extended or adjusted under 35 U.S.C. 154(b) by 1031 days.

(21) Appl. No.: 12/063,435

(22) PCT Filed: Oct. 24, 2006

(86) PCT No.: PCT/EP2006/067730
§ 371 (c)(1),
(2), (4) Date: Feb. 9, 2008

(87) PCT Pub. No.: WO2007/048798
PCT Pub. Date: May 3, 2007

(65) Prior Publication Data
US 2010/0138422 A1    Jun. 3, 2010

(30) Foreign Application Priority Data
Oct. 25, 2005  (EP) .................................. 05425752

(51) Int. Cl.
*G06K 9/00*    (2006.01)
(52) U.S. Cl. ....... 382/128; 358/1.15; 382/159; 382/181; 382/305; 707/740; 707/781; 707/802
(58) Field of Classification Search .................. None
See application file for complete search history.

(56) References Cited

U.S. PATENT DOCUMENTS

| 5,893,095 | A | * | 4/1999 | Jain et al. ............................... 1/1 |
| 6,611,846 | B1 | * | 8/2003 | Stoodley ....................... 707/740 |
| 2003/0140141 | A1 | | 7/2003 | Mullen | |
| 2004/0252871 | A1 | | 12/2004 | Tecotzky | |

FOREIGN PATENT DOCUMENTS

WO    WO 2005/055008    6/2005

OTHER PUBLICATIONS

Jing Bai et al.,"Design and Development of an interactive teleconsultation system over the World Wide Web," Jun. 2, 1999, vol. 2, pp. 74-79.*

Jim Bai et al: "Design and development of an interactive medical teleconsultation system over the World Wide Web," IEEE Transactions on Information Technology in Biomedicine, IEEE Service Center, Los Alamitos, CA, US, vol. 2, No. 2, Jun. 1999, pp. 74-79.

Mun S K: "Image Management and Communication (IMAC) in Radiology*" ONDE Electrique, Editions Chiron S.A. Paris, FR, vol. 71, No. 4, Jul. 1, 1991, pp. 26-31.

(Continued)

*Primary Examiner* — John Lee
(74) *Attorney, Agent, or Firm* — Themis Law

(57) ABSTRACT

An image processing system particularly for use with diagnostic images includes at least one processing unit, which receives digital images acquired by one or more imaging apparatus and provides output images, processed by an image processing program loaded in the memory of the processing unit and executed thereby, wherein the system includes a central service unit having an interface to be accessed by remote users, which connect to the central unit by remote communication.

17 Claims, 5 Drawing Sheets

OTHER PUBLICATIONS

Pereira J et al: "Integrated system to access-medical images in the Intranet and the extranet" 2nd JT EMBS-BMES Conf. 2002. Conf. Procdgs. 24th. Ann. Int'l Conf. of the Engrg in Medicine & Biology Society. Annual Fall Meeting, Houston, TX, Oct. 23-26, 2002, vol. 1, pp. 1887-1888.

Suenaga T et al: "A tele-instruction system for ultrasound probe operation based on shared ar technology" Procdgs of the 23rd. Ann. Int'l Conf. of the IEEE Engrg in Medicine & Biology Soc. 2001 Instanbul, Turkey, Oct. 25-28, 2001, vol. 1, Oct. 25, 2001, pp. 3765-3768.

Turk M et al: "Eigenfaces for Recognition," Journal of Cognitive Neuroscience, Cambridge, MA, US, vol. 3, No. 1, Jan. 1991, pp. 71-86.

* cited by examiner

IMAGE PROCESSING SYSTEM, PARTICULARLY FOR USE WITH DIAGNOSTIC IMAGES

BACKGROUND OF THE INVENTION

The invention relates to an image processing system, particularly for use with diagnostic images, comprising at least one processing unit, which receives digital images acquired by one or more imaging apparatus and provides output images, processed by means of an image processing program that is loaded in the memory of the processing unit and executed thereby.

SUMMARY OF THE INVENTION

Image processing methods and systems are known and used for various purposes, e.g. for industrial purposes, in the movie and television industries, in industrial and safety control systems and in the medical field, particularly to facilitate reading and interpretation tasks for the physician.

Particularly in the diagnostic field, these Computer Aided Diagnostic (CAD) methods and systems require important technical skills in terms of both imaging and image processing, and particularly processing by the required algorithms. Furthermore, several types of image processing algorithms and methods exist, having various purposes. Some of the processing methods use non expert algorithms, which are used to somehow prepare the image to further evaluation processing. The latter step requires the use of classification algorithms, such as clustering algorithms or predictive algorithms. Therefore, processing itself requires specially skilled operators, who can correctly apply the various types of image processing algorithms currently used by the processing methods. Correct use of these algorithms is critical to obtain reliable processing results for the physician to provide a correct diagnosis. A major problem consists in the so-called false positives, i.e. the identification of image regions that are evaluated by the processing system as potentially pathological, even though they do not correspond to a pathology. For certain pathologies, such as cancer, early detection of cancerous tissue is of the utmost importance; any minimally suspected region is further analyzed by more invasive investigation, such as biopsy or other similar methods. Therefore, false positive detection causes unreasonable time consumption and cost increase.

Regarding imaging, the personnel may be sufficiently trained to properly use imaging apparatus. Nevertheless, proper processing of acquired images, e.g. in hospitals, consulting rooms or in diagnostic laboratories, requires a special personnel team to be established, who are specifically trained for the development and use of the algorithms and corresponding programs required for image processing. This means that highly specialized personnel needs to be hired by health care organization, which involves considerable costs. Personnel training is not sufficient, because the team must be able to improve the processing tools with time, and adapt them to new techniques and standards. This means that the highly qualified personnel of the image processing management team has to be constantly retrained, which involves further costs.

Specifically regarding the classification algorithms to be used for image evaluation intended for recognition of image regions that may be interpreted as images of suspected pathological objects, these algorithms require a training step which is critical for their performance in terms of both computational speed and reliability of results. Much depends, in this case, on the database of known cases, which is used to train such algorithms. The more heterogeneous the database, the better the performance. These databases are typically quite expensive, because they not only contain a simple collection of known cases, but also require basic preparation. In one health care structure or organization, such as a hospital or the like, the number of new cases is limited to the patients treated by this organization, as well as to the instruments and imaging techniques available in such health care organization and to the personnel resources thereof. Therefore, the number of cases that can be used for constant updating of the classification capabilities of classification algorithms is limited to the knowledge that is acquired in the health care organization.

These problems exist for any type of clinical investigation, such as X-ray mammography or contrast enhanced Magnetic Resonance Mammography, which will correspond to different types of images. For each clinical investigation, a dedicated analysis algorithm is needed, and this requires the users to be in turn trained on the specific system to be used for each clinical investigation.

The invention has the object of providing a system that obviates the above drawbacks, by turning the image processing step into a simple service step, thereby requiring neither specialized personnel in the health care organization, nor the purchase of image processing systems, and avoiding the costs involved by maintaining such systems always efficient and up-to-date, by purchasing new software modules or software improvements.

A further object of the present invention consists in allowing a more efficient and rapid way of furnishing the results of the image processing unit by limiting the number of skilled persons necessary for processing the images.

The invention has the further object of facilitating the payment step, by avoiding the need of making a considerable capital investment, and allowing a recording of expenses as professional services and pay them based on the actual use thereof.

The invention further allows health care organizations not to depend on installation, maintenance and service interventions provided by software companies.

The invention fulfills the above objects by providing a system as described hereinbefore, wherein the image processing system, particularly for use with diagnostic images, comprises at least one processing unit, which receives digital images acquired by one or more imaging apparatus and provides output images, processed by means of an image processing program loaded in the memory of the processing unit and executed thereby. The system includes a central service unit, comprising an interface to be accessed by remote users, which connects to such central unit by remote communication means for the transmission of one or more of the said images to the said processing unit, the processing unit executes automatically the image processing program on the one or more images.

Thanks to the invention the system automatically recognizes which kind of images has been sent by the user and automatically starts the processing of the image or images received, by choosing the image processing tools suited for the images either from the point of view of the method used for acquiring the image and also from the point of view of the object imaged and of the diagnostic purpose of the image. No specialized service person is needed for carrying out this steps and the user itself does not need to have any kind of skill in image processing.

One or more feedback messages can be sent automatically by the system to the user requesting the service and sending the images. In particular the system by analyzing the images sent by the user can inform the user of the correct receipt, of the fact that the image quality is sufficient or insufficient for carrying out a successful processing, of the time needed for processing and of possible options of processing which the user can select depending on further information about the aim of the processing requested by the user and which information was lacking in the originally sent message.

According to a further improvement the system provides for the fact that a) in the memory of the central processing unit there are stored and/or loadable more than one image processing program, each one of these image processing program being capable of executing a different operation;

b) the different image processing programs may be executable in a separate way or as a sequence of operation steps on at least one image;

c) a selection and execution program is provided which is stored or loadable in the memory of the processing unit and which is executed by the processing unit for selecting one or more image processing programs and for causing their execution;

d) the selection and execution program further analyzes the image data of the images received by the central processing unit and automatically recognizes the kind of the image processing programs to be used and the order in which the image processing programs has to be carried out on the image or images.

The central image processing unit is composed of modules, each consisting of hardware/software operating units.

At least some or all of said operating units have a dedicated processor and a dedicated memory area, which contains the code of a processing program incorporating the instructions for executing the operating functions of said operating units.

Otherwise, at least some or all of said operating units have a dedicated memory area, which contains the code of a processing program incorporating the instructions for executing the operating functions of said operating units, which code is executed upon request by a central processing hardware unit.

According to a preferred embodiment, the system includes a central control system or agent which executes a logic system management program to coordinate specific remote client identification functions and to check service login codes, to charge service costs, to coordinate subunits for storing received image data, subunits for image processing, subunits for managing and updating the database that is used to train the processing algorithms, particularly the classification algorithms, and subunits for generating graphic and alphanumeric evaluation reports and for transmitting or otherwise providing them to the remote clients.

According to yet another feature of the invention, the processing subunits include a processing management unit, the so-called CAD engine, which prepares image data for processing by an image processing unit, known as ALGO, which executes the code for applying the image processing algorithms and also manages access to the image processing unit. Furthermore, the processing management unit manages and coordinates access to the training database by the image processing unit and database update.

According to an advantageous embodiment, the central control system generates a database of cases to be processed, in which identification codes are used to uniquely identify the remote client that transmitted the images and the specific case whereto the images are related, while automatically anonymizing said specific case and patient data.

The data records to be processed include image data, imaging mode and imaging technique data, as well as patient personal and historical data and relevant patient anamnestic data.

The central control system includes means for checking the authorizations of the remote client/s and generates a catalog of cases transmitted by said client/s for processing, which cases are uniquely identified by the remote client identification code or by the case identification code.

The authorization means enable transmission or access by the processing subunits to the database of cases to be processed.

The processing subunits generate image processing output files to be transmitted to the central control system, which in turn has means for generating an output catalog of processed cases, in which each item is associated to an image processing output file related to such case.

Advantageously, the central control system automatically generates a processing complete signal which is transmitted to the appropriate remote client/s by communication means.

The processing output files may be also integrally transmitted to the remote clients or the latter may be allowed to access the output catalog of processed cases.

Advantageously, the central control system generates a preview file of processing results for client-specific cases in the output catalog, which allows each remote client to display the processed images and/or the processing data in alphanumeric form.

Furthermore, the central control system has means for allowing remote clients to only select the processing results of specific cases and/or specific images of processed cases, and to request the transmission of full processing results relating to said specific selected images.

Such transmission may occur by using communication means or portable digital file storage media or by printing such processing results on paper, or in any other possible form.

The users may make the final diagnosis data (resulting from biopsy or surgical sample analysis) available, through their client, for each of CAD processed cases. To this end, the central control unit controls the unit that manages the update of the image processing algorithm training database. This unit retrieves from the catalog of processed cases, the cases allowed by the clients for inclusion in a training database updating program, and consequently updates such database by using the system output and the final diagnosis data, which will be regarded as "gold standard".

The subsystem analyzes the new cases to be added to the training database and generates records to be added to the training database in the specific format required for said database.

Thanks to the above features, the system of this invention allows central control of image processing, with no excessive burden either in terms of costs or in terms of organization tasks for health care organizations that need to perform diagnostic image processing.

The technical advantage consists in that the central system may fully utilize the available computational capabilities and the processing algorithms, especially the classification algorithms, are applied to a very large number of different cases, which allows an optimized utilization of the classification capabilities and performances thereof.

Furthermore, thanks to the clients who allow inclusion of treated cases in the classification algorithm training database, while also providing cross-checking clinical analyses, which may confirm or deny the classification results obtained by the algorithm service, new cases are constantly added to the training database at a very low cost, thereby improving the performances of processing algorithms. From a technical point of view, when many remote clients authorize the use of the data transmitted to the service for processing, a very heterogeneous training database is obtained, both due to the difference of the diagnostic cases being treated, and to the difference of operators, apparatus and capabilities by which image data is being acquired, whereby the basic information has a considerable diversification and allows improving classification and prediction capabilities. This advantage cannot be obtained if image processing is performed locally and independently by each client.

Also, central processing assures absolute reliability of any new case data to be used for updating the training database, therefore unlike the condition in which updating occurs by an exchange of database records locally generated by the clients, this record data need not be checked for correctness and consistency. Conversely, the records obtained by remote clients that perform independent processing within their own organization may include processing errors caused by poor personnel skills or faults in local remote client systems, whereby any inclusion thereof in a training database without an accurate check for reliability and consistency may cause the classification and processing performances to be worsened instead of improved.

From the point of view of users, i.e. the remote clients, on-line access to processing results allows a reduction of costs in terms of both processing and storage of redundant data, which is not essential for the requested diagnostic assistance, while a substantial trace of the data set remains in the central system.

Further improvements and variants of the invention will form the subject of the dependent claims.

BRIEF DESCRIPTION OF THE DRAWINGS

The characteristics of the inventive system and the advantages derived therefrom will appear more clearly from the following description of one embodiment, with reference to the annexed drawings, in which.

DETAILED DESCRIPTION OF EMBODIMENTS OF THE INVENTION

Figure 1:
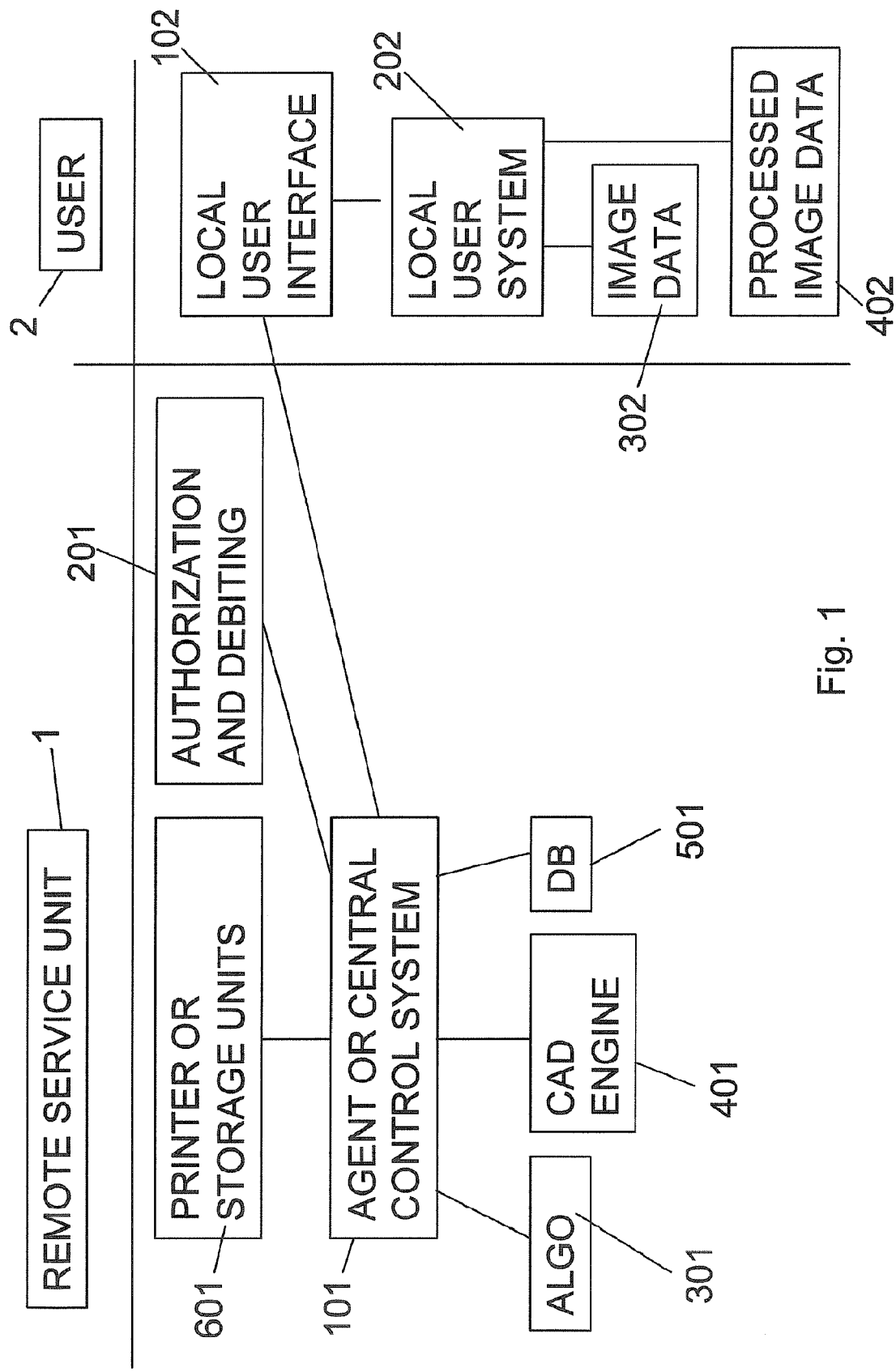
FIG. 1 is a general block diagram of a system according to the present invention.

FIG. 1 is a block diagram of a system according to the present invention. The left side of the Figure represents the remote service unit 1, which performs central image processing functions. The right side represents a user 2, who is at a local service center. Several local users, one of which is only represented here, may connect simultaneously to the remote service unit to request image processing services.

The remote service unit 1 comprises a central control system 101 which performs a logic control program for coordinated management of several different functions. This central control system, or agent, controls the unit 201 for authorizing accesses and charging service costs to each user. The image processing units are referred to as CAD engine 401, ALGO 301 and DB 501. Furthermore, the agent unit or central control system 101 controls the storage and printer units 601 and the units, not shown in detail, for communication with the users, who have in turn a local user communication interface 102, which is used by the local user system to connect the local user system 202 with the remote service unit 1.

The local user system 202 receives or collects locally acquired images, provided by any imaging apparatus of whatever kind, such as a MRI apparatus, an ultrasonic imaging apparatus, a radiographic imaging apparatus and the like. Images are provided in the form of digital image data 302 and are transmitted to the remote service system which checks that the user is authorized to access the service and allows image data reception and processing. The processed digital images and/or any graphical and/or alphanumeric reports associated thereto are transmitted to the local user system which stores them in any format or form, as schematically shown by block 402. All these tasks are performed under the control of the agent or central control system 101.

Figure 2:
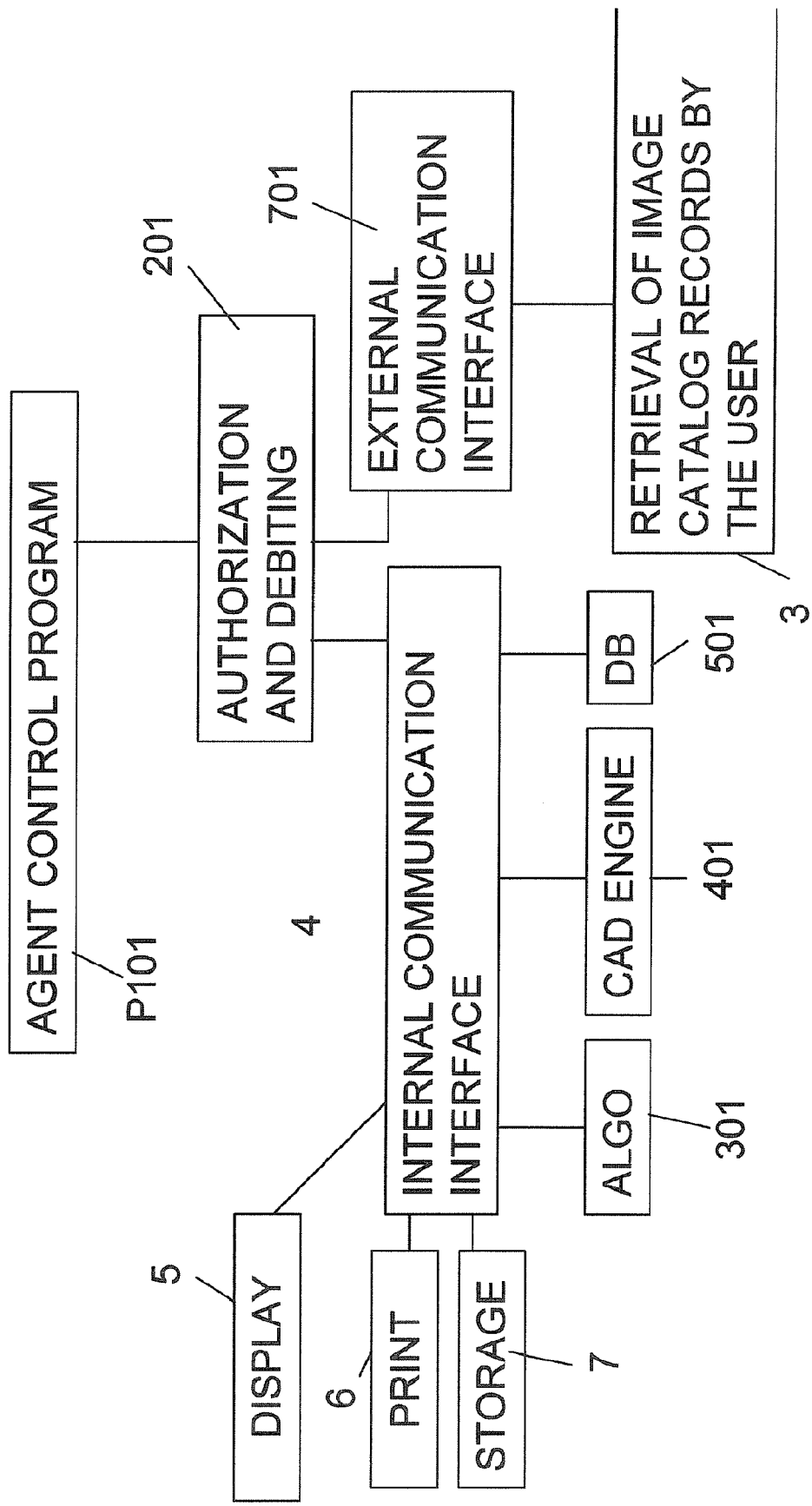
FIG. 2 is a more specific block diagram of the central image processing system.

FIG. 2 is a block diagram of the remote service unit 1. An agent control program p101 of the agent unit or central control system 1 supervises the authorization and debiting functions of the unit 201. Authorization occurs by user login authentication. A login request also automatically causes the corresponding user debit management programs to be started.

Once the agent control program receives information about successful authorization and opening of accounting procedures, the external communication interface 701 is enabled, which allows the user to upload the image data files for processing and to receive the image processing results, as shown by block 3.

Still after user access authorization by the unit 201, the agent control program enables an internal communication interface 4, allowing communication between the display units 5, the printer units 6, the storage units 7 and the image processing units, i.e. ALGO 301, CAD engine 401 and database 501.

Image data is then processed and the processing results are stored and made available to the user.

In an advantageous embodiment of the present invention, the remote service unit does not transmit all the processing results, but only makes processing result files available for each image uploaded by the user, adding a notice thereto. Depending on such notice, the user will access the retrieval service and only download the result files for the desired images. The service is charged as a function of the number of files that are actually downloaded by the user.

Advantageously, to simplify the download of image processing result files, the remote service unit generates, by its agent control program, a catalog of image data files transmitted by users for processing, and after processing the catalog is updated with the corresponding image data processing result files. A further simplification may be obtained by adding graphic or alphanumeric processing result previews to the catalog, such as a miniaturized processed images and/or statistic classification reliability data for the objects detected in the image and deemed to be of interest for the user.

Figure 3:
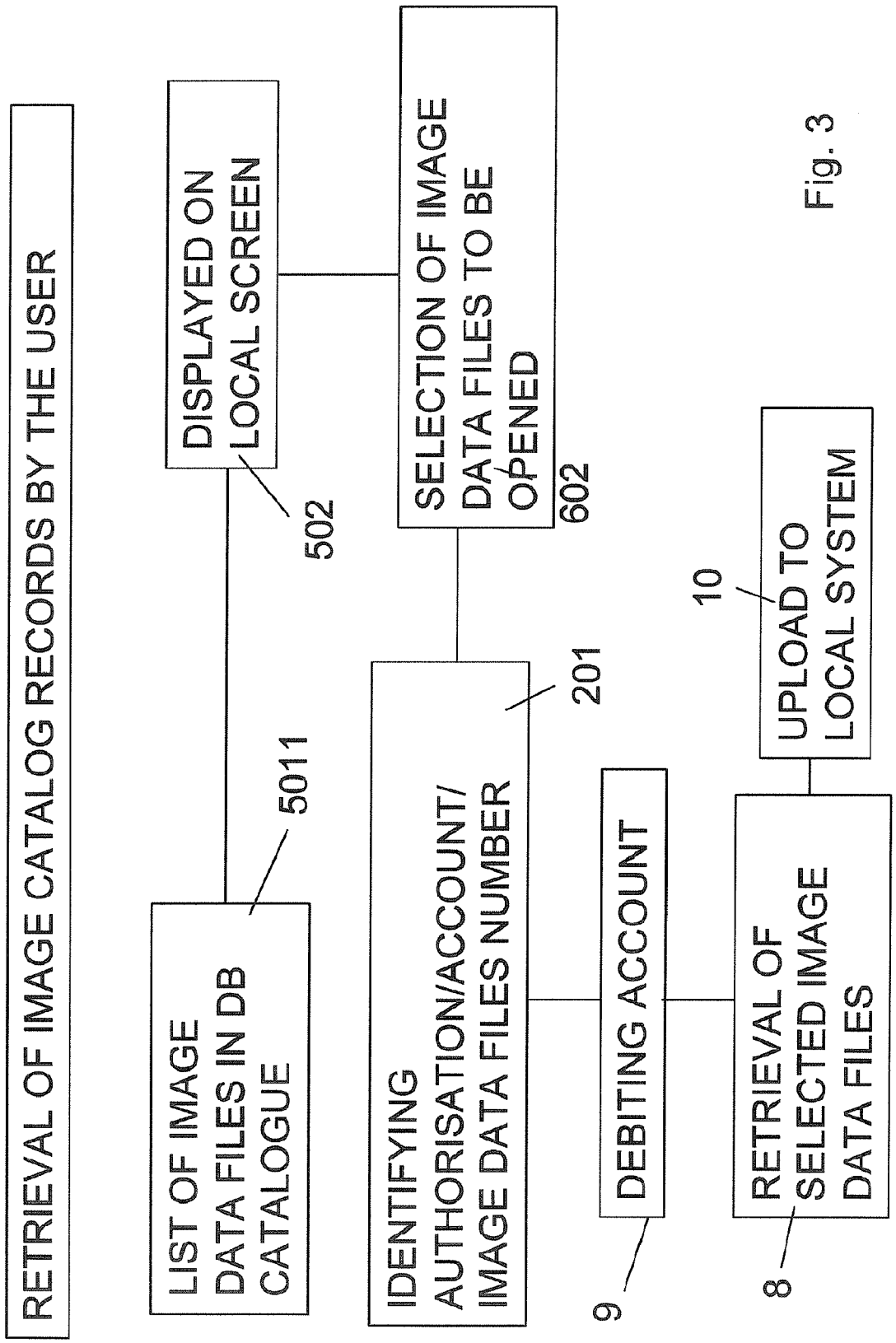
FIG. 3 is a block diagram of the system for accessing the processing results.

FIG. 3 shows the steps of result file downloads by users in greater detail.

Once a user is connected to the remote service unit, he/she can access a list of image data files in a catalog of an image processing result database 5011. The images corresponding to each user, identified by an ID code of the latter, may be freely displayed on a local monitor 502 of the local user system 202. The images processed by the remote service unit may be displayed in combination with alphanumeric reports, indicating the statistic reliability of the results of processing and classification of the objects detected in the corresponding images being displayed. Then the user may make a selection by using the means 602. Now the authorization and debiting unit 201 controls download authorizations and charges the cost for each processing result file selected by the user. The selections made by the user are uniquely identified thanks to a unique ID code of the original image data and the associated processing result files. After a successful debiting step 9, the agent control program p101 enables access to the processing result files selected by the user, as shown by block 8 and uploads them to the local user system, as shown by block 10.

It is worth noting that, when requested, the processing result files for one or more images may be also transmitted by other means, such as on portable storage media, i.e. floppy disks, CD-ROM, DVD-ROM and the like, or even printed on paper.

Figure 4:
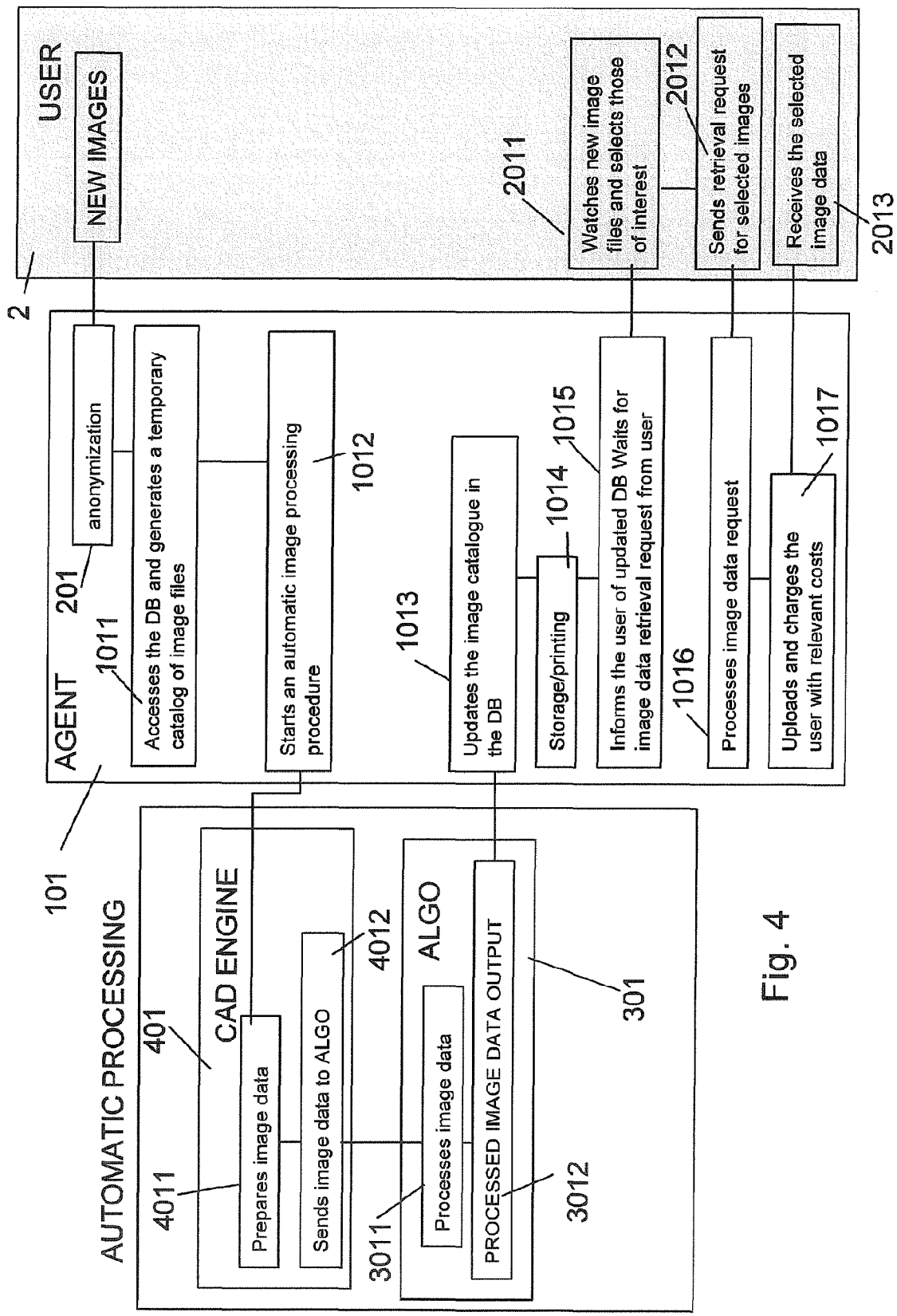
FIG. 4 is a block diagram of the operating steps of system according to the present invention.

FIG. 4 is a more detailed functional block diagram of an embodiment of the inventive system. Three large blocks may be found in this figure, and the first represents the automatic image processing module, which performs processing tasks using non-expert algorithm-based methods, and further expert or classification algorithm-based processing tasks. The second large block represents the agent or central control system 101, which performs the remote service unit tasks, whereas the third large block represents the user 2, in this case one or more users.

Each user 2 having a valid login for authorized paying access to the remote service unit, may connect to such unit to upload new images 302 in the form of digital image data. The agent or central control system 101 uses various devices controlled thereby, e.g. an authorization and debiting unit 201, to anonymize the image data and any personal patient data and/or patient history data. This is possible, for instance, by using encryption means, whose key is the user ID, as well as a code uniquely assigned to each image or to each set of images. Other currently available systems are also possible.

Once the image data has been anonymized, in step 1011 the agent or central control system 101 allows the image data to access the database 501 of image data to be processed, while generating a temporary catalog file and then, in step 1012, controls the automatic image processing units 401, 301 to start the processing step.

The image data in the database 501 that is found in the temporary catalog is first processed by the CAD engine 401. In step 4011, the latter prepares the image data for further processing, for instance by encoding such image data to make them readable by the processing algorithms ALGO 301 and, in step 4012, it sends the prepared image data to said processing unit ALGO 301. In step 3011 the image data is processed by the algorithms of the ALGO unit 301. These algorithms may be one or more algorithms designed for sequential and/or parallel application in any chain of processing steps and, in step 3012, they provide a processed image data output as a processing result file containing the processed image data itself and/or graphic and/or alphanumeric processing reports. The agent or central control system 101 is informed that processing has been completed and, in step 1013, it updates the database and the corresponding catalog.

Thus, the processing result files are stored and/or printed 1014. In step 1015, the agent or central control system 101 generates a Processing completed message, which is transmitted to the user that corresponds to the ID code of the processed images. Now the remote service unit will wait for request. The user may then connect service unit and access, as shown reference to FIG. 3 and step 2011, processing result files corresponding a specific user to the remote in detail with the catalog of to his/her own user ID and the corresponding previews. Based on this information, the user can send, in 2012, a request for downloading the processing result files for certain desired images. In step 1016, the agent or central control system 101 processes the request and charges the user with the costs for the requested processing result files, then it sends 1017 the user the selected processing result files, which are received 2013 by the user 2.

It is worth noting that, thanks to this system, a highly selected personnel team is only needed at the remote service unit, and their cost is distributed among a large number of users, their task being limited to the supervision and management of specific administration and image processing operations. It may be further easily noted that a huge number of cases are made available to the remote service unit and after being processed such cases can be added to the training database of expert algorithms, such as classification algorithms or predictive algorithms, whose performances critically depend on the number of known cases on which their training is based.

Also, the base material, i.e. images, is received from a large number of users, and is highly heterogeneous in terms of quality features, and this definitely helps in improving processing performance.

Thanks to this system, a user feedback step may be provided in which users, based on the processing result files for certain images, decide to perform deeper diagnostic tests and can upload processing result data to confirm the results obtained by image processing only.

Figure 5:
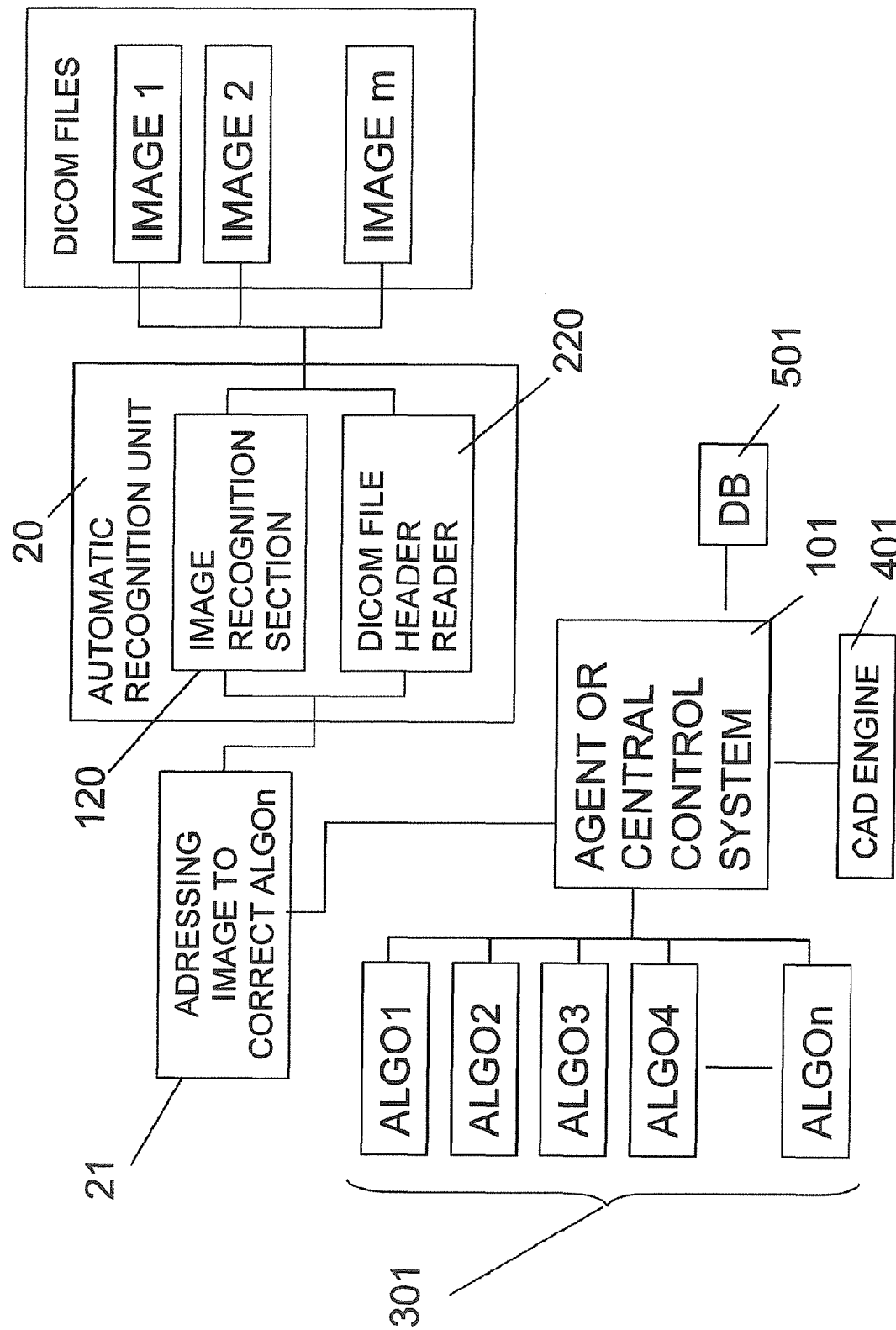
FIG. 5 is a block diagram of a further improvement, which includes means for identifying the object reproduced in the image and processing it by a specific specialized algorithm.

Referring to FIG. 5, a variant embodiment is shown, which further improves the inventive system.

According to this improvement, the system has an automatic recognition unit, for instance a software component, which automatically recognizes the image and investigation type, and therefore the anatomic part, i.e. the organ, anatomic region or a portion thereof under examination, that has been imaged. The recognition unit is based on a trained expert system, which uses, as recognition features, both the diagnostic image data and the 'header' data of files, particularly of dicom files, which are typically used for medical data. More particularly, recognition is performed by algorithms which are characterized by an intelligent system based on an adaptation of the Eigenface method for face recognition. The algorithm uses a trained intelligent system based both on Eigenimages and on actual image data, such as the grey scale tones of the original image or of a transformation thereof, and characteristics deriving from skeletonizing algorithms. Thus, the purpose of this function is to recognize and sort various image types, by organs or anatomic regions under examination and/or possibly by imaging methods. Therefore, the recognition unit operates on two levels, one of which is related to the organ or anatomic region or portion thereof being imaged, whereas the other level constitutes a second decision line which identifies which type of investigation has been used from the information contained in the header of the dicom file, e.g. by reading the spatial resolution, the possible provision of contrast enhancement and the imaging technique being used. Hence, the automatic recognition unit of the system comprises two subunits, one of which is a unit designed to recognize the imaged object directly from the image, whereas the other is a unit designed to recognize the type of investigation, i.e. image, from the spatial resolution, the presence or lack of contrast enhancement, the imaging technique being used and other parameters that are specific to the imaging technique and image quality. While the first unit uses image recognition algorithms, the second unit typically reads the investigation type data from the dicom files that are typically used in the medical field.

The combination of these two levels affords automatic image recognition, whereby such images may be provided to one or more processing algorithms specifically designed for processing various organs or anatomic regions or portions thereof and/or to various processing algorithms specifically designed for processing various image types, differing in terms of image features, e.g. spatial resolution, presence or lack of contrast enhancement, imaging technique being used.

FIG. 5 is a block diagram of one embodiment. Here, several different images are shown, denoted by Image 1 to Image m, in DICOM format. This file format is a standard for digital storage of data, images or other information in medical imaging. DICOM image files are read by the recognition unit 20, which comprises a section 120 for recognizing the imaged object, i.e. the organ and/or the anatomic region and/or a portion thereof. Another section 220 operates in parallel with the former to read the DICOM file header, which generally includes information about the imaging method, such as the imaging mode, the resolution, the presence or lack of contrast enhancement and other information about the imaging techniques, which may be of interest for image analysis and interpretation.

The two sections 120, 220 carry out two parallel decision processes and, based on their results, the image files are addressed by the agent 101 to processing by one of a number of processing algorithms 301 which have been prepared in the system and are specifically designed for processing various types of diagnostic images both as regards the imaged object and the image features related to the imaging techniques and modes being used.

In certain cases, each image may be addressed to simultaneous processing by two or more algorithms. In this case, the result file will include separate processing information for each algorithm, and possibly a prediction of diagnostic hypotheses based on the combination of processing results of the different processing algorithms.

Regarding the section 220 of the recognition unit, no difficulty arises from DICOM header reading by the recognition algorithm, thanks to the fact that the numeric data or unique identification of the imaging type is coded and easily recognizable by software. However, the identification of the imaged object, i.e. the organ or portion thereof and/or the anatomic region or portion thereof, requires a more complex process and, as mentioned above, utilizes specific face recognition algorithms, which are typically used in automatic recognition of biometric data.

Referring to automatic recognition of imaged objects, a number of well-known methods may be used, such as the Content-Based Image Retrieval (CBIR) method, also known as Query By Image Content (QBIC) and Content-Based Visual Information Retrieval (CBVIR).

These methods involve the use of computer vision techniques in Image Retrieval, i.e. to query a large database of images for specific digital images. The term "content-based" means that the query is based on image content and not on human-applied metadata such as keywords and query words. The software that incorporates such a method is known as "Content-Based Image Retrieval System" (CBIRS).

An ideal CBIR system includes the so-called semantic query. This operation is relatively complicated and CBIR systems generally use lower-order features, such as textures, colors and shapes. Nevertheless, certain systems, such as the so-called face recognition systems, use higher-order features.

The CBIR or QBIC or CBVIR systems are described in greater detail in the following documents: SIMPLIcity: Semantics-Sensitive Integrated Matching for Picture Libraries (Wang, Li, and Wiederhold, 2001], Automatic Linguistic Indexing of Pictures by a Statistical Modeling Approach (Li and Wang, 2003], System for Screening Objectionable Images (Wang et al., 1998), Video google: A text retrieval approach to object matching in videos (Sivic & Zisserman, 2003), Names and Faces in the News (Berg et al, 2004), FACERET: An Interactive Face Retrieval System Based on Self-Organizing Maps (Ruiz-del-Solar et al, 2002), Costume: A New Feature for Automatic Video Content Indexing (Jaffre 2005), Finding Naked People (Fleck et al, 1996), Automatic Face Recognition for Film Character Retrieval in Feature-Length Films (Arandjelovic & Zisserman, 2005) which are to be considered incorporated herein by reference.

Face recognition systems are computer software for automatic identification of persons from a digital image. Recognition occurs by comparing an image of a person with a database of face images. Face recognition algorithms include the so-called eigenfaces, fisherfaces, the hidden Markov model and the Neuronal Motivated Dynamic Link Matching.

"Eigenfaces" are a set of eigenvectors derived from the covariance matrix of the probability distribution of the high-dimensional vector space of possible faces of human beings. These eigenvectors are used in the computer vision problem of human face recognition.

In face recognition, eigenfaces are a set of "standardized face ingredients" derived from statistical analysis of many face images. Any human face can be considered to be a combination of these standard faces.

To generate a set of eigenfaces, a large set of human face images, taken under the same lighting conditions, are normalized to line up the eyes and mouths. These images are then sampled at the same resolution and treated as vectors whose size corresponds to the product of the number of lines and columns of the sampled image matrix and the components of which vector are the values of the individual pixels of the sampled image matrix. The eigenvectors of the covariance matrix of the statistical distribution of face image vectors are then extracted.

When properly weighted, eigenfaces can create an approximate gray-scale rendering of a human face and are not only used in face recognition but also for image compression purposes.

A more detailed description of eigenfaces may be found in the following publications:

L. Sirovich and M. Kirby (1987). "Low-dimensional procedure for the characterization of human faces". Journal of the Optical Society of America A 4:519-524, M. Kirby and L. Sirovich (1990). "Application of the Karhunen-Loeve procedure for the characterization of human faces". IEEE Transactions on Pattern analysis and Machine Intelligence 12 (1): 103-108, M. Turk and A. Pentland. (1991). "Face recognition using eigenfaces". Proc. IEEE Conference on Computer Vision and Pattern Recognition, 586-591, M. Turk and A. Pentland (1991). "Eigenfaces for recognition". Journal of Cognitive Neuroscience 3 (1): 71-86, A. Pentland, B. Moghaddam, T. Starner, O. Oliyide, and M. Turk. (1993). "View-based and modular Eigenspaces for face recognition". Technical Report 245, M.I.T Media Lab, which also are to be considered incorporated herein by reference.

In the system of this invention, the principle of "eigenfaces" may be used for automatic recognition of an imaged object. Here, the database 501 of the processing section may be used to generate equivalents of "eigenfaces", which relate in this case to organs or portions thereof or anatomic regions or portions thereof. The methods may be as those described above and currently used for generation of the database of eigenfaces in face recognition.

Once a database of "eigenfaces" of organs or portions thereof or anatomic regions or portions thereof has been generated, the combinations of eigenfaces which characterize a particular organ may be determined, therefore for each image that is uploaded for processing an eigenface composition may be determined, whereupon this combination may be compared with that defined from the database images to automatically determine which organ or part thereof or which anatomic region or part thereof is being imaged. These steps may be advantageously carried out using a classification algorithm, such as a clustering algorithm or a predictive algorithm.

In this case, the predictive algorithm is trained using the database of known cases which forms the base for the inventive system, and using the combinations of "eigenfaces" which characterize the individual images of such database. Once the clustering algorithm or predictive algorithm, such as an artificial neural network, has been trained, if an input image is uploaded for recognition, the algorithm provides the eigenface decomposition of the image and determines that the image belongs to the class of a particular organ or portion thereof or a particular anatomic region or a portion thereof.

In this case, the output of the predictive algorithm still has to be submitted to a comparative check with the various combinations of eigenfaces obtained for each image of the database and for each organ or anatomic regions or portions thereof reproduced in these images.

The predictive or clustering algorithm may be structured in such a manner that its output directly consists in the evaluation of the imaged object, and generates a direct association between the combination of eigenfaces obtained at the output of the predictive algorithm and the type of organ or anatomic district or a portion thereof, which is uniquely associated to said combination of eigenfaces.

The invention claimed is:

1. A system for processing diagnostic images comprising:
   a central computer service unit configured to,
   authorize access by a user,
   debit the user for processing the diagnostic images,
   receive, process and store the diagnostic images, and
   enable the user to retrieve data of one or more of the diagnostic images after the processing; and
   a local user interface unit comprising hardware configured to enable the user to,
   communicate remotely with the central computer service unit,
   request authorization for the access by the user,
   upload the diagnostic images to be processed to the central computer service unit, and
   access the central computer service unit to receive at least some of the data of at least some of the diagnostic images after the processing,
   wherein the central computer service unit is configured to receive, process and store the diagnostic images provided by a plurality of local users, such to provide a centralized processing capability to the plurality of local users,
   wherein the central computer service unit is configured to process the diagnostic images by activating a computer aided diagnostic (CAD) subunit to prepare the diagnostic images for the processing and an image processing subunit to apply one or more image processing programs to the diagnostic images,
   wherein the central computer service unit further comprises:
   a coordinating subunit performing remote user identification, checking user login codes, and debiting service costs to the user;
   a database management subunit managing and updating an image database that is used to train the one or more image processing programs; and
   a reporting subunit generating graphic and alphanumeric evaluation reports of the diagnostic images after the processing, such that the evaluation reports are provided to the user on a video display, on a digital file storage medium, or in paper form, and
   wherein the one or more image processing programs comprise a plurality of image processing algorithms, each designed to process at least one of the diagnostic images related to a specific organ or a portion thereof, or a specific anatomic region or a portion thereof, and
   wherein the image processing subunit comprises an automatic image recognition subunit configured to identify the imaged organ or the portion thereof, or the imaged anatomic region or the portion thereof, and to address the at least one of the diagnostic images to be processed to one or more of the plurality of processing algorithms that are specifically designed to process images of the imaged organ or the portion thereof, or the imaged anatomic region or the portion thereof as recognized by the image recognition subunit.

2. The system of claim 1, wherein the CAD subunit and the image processing subunit each comprise a dedicated computer processor and a dedicated memory area.

3. The system of claim 1, wherein CAD subunit is configured to coordinate access to the image database by the image processing subunit.

4. The system of claim 1, wherein the database management subunit is configured to update the image database by adding processed cases and by adding final results that have been clinically verified by different users.

5. The system of claim 1, wherein the central computer service unit is configured to generate a database of cases to be processed, wherein identification codes are used to univocally identify the user who has transmitted the diagnostic images and a specific case to which the diagnostic images are related while automatically anonymizing the specific case and related patient data.

6. The system of claim 1, wherein the diagnostic images to be processed are provided with one or more of image data, imaging mode data, imaging technique data, biological data of a patient, historical data of the patient, or anamnestic data of the patient.

7. The system of claim 1, wherein the at least some of the data of at least some of the diagnostic images are stored in an output database catalog of processed cases, wherein the at least some of the data is associated to an output file related to a patient of interest.

8. The system of claim 7, wherein the local user interface unit is configured to receive the at least some of the data by accessing the output database catalog of processed cases.

9. The system of claim 7, wherein the central computer service unit is further configured to provide the local user interface unit with a preview file of processing results for the diagnostic images in the output database catalog, thereby enabling the user to display the at least some of the data of at least some of the diagnostic images in alphanumeric form.

10. The system of claim 1, wherein the central computer service unit is further configured to generate and send to the user a processing complete signal after the processing the diagnostic images.

11. The system of claim 1, wherein the central computer service unit is configured to debit the user based on the data actually retrieved by the user.

12. The system of claim 1,
wherein the diagnostic images to be processed are provided in DICOM format,
wherein the image recognition subunit comprises an image recognition section and a DICOM file header reading section and is configured to extract one or more of imaging method, image resolution, or contrast enhancement provision information, and
wherein the plurality of processing algorithms comprises algorithms specifically designed for image processing related to the imaging method, image resolution, or contrast enhancement provision information, and
wherein each diagnostic image in DICOM format is addressed to one of the plurality of processing algorithms that is specifically designed for the image processing for the imaging method, image resolution, or contrast enhancement provision identified for the diagnostic image in DICOM format to be processed.

13. The system of claim 12, wherein the one or more of the plurality of processing algorithms are two or more of the plurality of processing algorithms, and wherein a processing result is determined by combining results of the two or more of the plurality of processing algorithms.

14. The system of claim 12, wherein the image recognition subunit or the image recognition section is a Content-Based Image Retrieval (CBIR) system.

15. The system of claim 14, wherein the CBIR system uses sets of eigenfaces for identifying the organ or the portion thereof, or the specific anatomic region or the portion thereof that have been imaged.

16. The system of claim 15, wherein the eigenfaces are generated by transforming each image of the image database into vectors having size corresponding to a product of number of lines and columns of a sampled image matrix, wherein components of the vectors are values of individual pixels of the image, and wherein the eigenfaces are eigenvectors of a covariance matrix of a statistical distribution of the vectors of the diagnostic images of organs or portions thereof, or of anatomic regions or portions thereof.

17. The system of claim 16, wherein a classification algorithm is used to automatically determine the imaged organ or the portion thereof or the imaged anatomic region or the portion thereof, the classification algorithm being trained with the image database, and a corresponding set of eigenfaces corresponding to each image of the image database, wherein the imaged organ or the portion thereof is determined by identifying, with the classification algorithm, a combination of eigenfaces that characterizes the one of the diagnostic images, and by comparing the combination of eigenfaces with a typical combinations of eigenfaces for images of the image database representing the specific organ or the portion thereof, or the specific anatomic region or the portion thereof.

* * * * *